United States Patent
Soffiati et al.

(10) Patent No.: US 7,186,761 B2
(45) Date of Patent: Mar. 6, 2007

(54) BONE CEMENT CONTAINING COATED RADIOPAQUE PARTICLES AND ITS PREPARATION

(75) Inventors: Renzo Soffiati, Nogara (IT); Pierfrancesco Robotti, Verona (IT)

(73) Assignee: Tecres, S.p.A., Sommacampagna (IT)

( * ) Notice: Subject to any disclaimer, the term of this patent is extended or adjusted under 35 U.S.C. 154(b) by 360 days.

(21) Appl. No.: 10/475,374

(22) PCT Filed: May 28, 2002

(86) PCT No.: PCT/IB02/01860

§ 371 (c)(1), (2), (4) Date: Oct. 20, 2003

(87) PCT Pub. No.: WO02/096474

PCT Pub. Date: Dec. 5, 2002

(65) Prior Publication Data

US 2004/0157952 A1    Aug. 12, 2004

(30) Foreign Application Priority Data

May 30, 2001  (IT) ............................ VI2001A0126

(51) Int. Cl.
*A61K 6/083* (2006.01)
*A61C 5/00* (2006.01)
*C08K 3/08* (2006.01)
*C08K 9/10* (2006.01)

(52) U.S. Cl. ...................... 523/117; 523/200; 523/210; 524/439; 433/228.1; 977/DIG. 1

(58) Field of Classification Search ................ 523/117, 523/200, 210; 524/439
See application file for complete search history.

(56) References Cited

U.S. PATENT DOCUMENTS

| 5,289,831 A | * | 3/1994 | Bosley .................. 128/899 |
|---|---|---|---|
| 5,336,699 A | | 8/1994 | Cooke et al. |
| 5,574,075 A | | 11/1996 | Draenert |
| 5,795,922 A | * | 8/1998 | Demian et al. ............. 523/117 |
| 6,355,705 B1 | * | 3/2002 | Bond et al. ................. 523/118 |
| 6,585,755 B2 | * | 7/2003 | Jackson et al. ............ 623/1.15 |

FOREIGN PATENT DOCUMENTS

| EP | 0 041 614 | 12/1981 |
|---|---|---|
| WO | PCT/EP01/01746 | 9/1991 |
| WO | PCT/US98/21576 | 10/1998 |

* cited by examiner

*Primary Examiner*—Tae H Yoon
(74) *Attorney, Agent, or Firm*—R. Neil Sudol; Henry D. Coleman; William J. Sapone

(57) ABSTRACT

An acrylic radiopaque bone cement for orthopedic use comprises a solid phase composed of a mixture of at least one poly(methyl acrylate)-based polymer, one free-radical polymerization initiator and one or more substances opaque to X-rays, and a liquid phase substantially composed of a mixture of at least one monomer, one accelerator and one stabilizer. The radiopaque substances comprise metallic tungsten and tantalum particles, compounds or mixtures thereof, covered with a polymer coating compatible with said bone cement. The coating layer of the particles of radiopaque substances is an acrylic polymer based on poly (methyl methacrylate). The amount of radiopacifying element is between 1% and 20% by weight, relative to the solid phase, preferably between 2% and 5% by weight, relative to the solid phase. The solid phase may additionally comprise one or more pharmacologically active substances. The method for its preparation consists in preparing the radiopacifying material by coating the metal particles with a layer of a polymer which is compatible with the matrix and exhibits oxygen barrier properties such that said layer does not dissolve completely in the liquid phase so as to keep its oxygen barrier properties at least partly unchanged.

20 Claims, 4 Drawing Sheets

Powder of Tantalum un-coated    mag=1000x

FIG. 3

Powder of Tantalum un-coated    mag=3000x

FIG. 4

Powder of Tantalum un-coated mag=10000x

FIG. 5

Powder of Tantalum coated with the Poly (methyl methacrylate)  mag=3000x

FIG. 6

Powder of Tantalum coated with the Poly (methyl methacrylate)  mag=10000x

FIG. 7

BONE CEMENT CONTAINING COATED RADIOPAQUE PARTICLES AND ITS PREPARATION

BACKGROUND OF THE INVENTION

1. Technical Field

The present invention relates to the field of bone cements and specifically concerns a radiopaque acrylic bone cement having improved mechanical characteristics and a method for its preparation.

The bone cement according to the invention is therefore suitable for use advantageously in surgery where the combination of a high degree of radiopacity and notable mechanical strength are required.

More particularly, the present invention relates to a bone cement which is suitable in particular for applications in vertebroplasty, cranioplasty, maxillofacial surgery and for fixing prostheses in orthopaedic surgery.

2. Background Art

In the orthopaedic surgery sector, bone cements composed of a mixture of resins biocompatible with the bone tissues are known and commonly used for stably fixing prostheses of different types in a wide range of locations on the skeleton or for restoring the continuity of tissues.

The most commonly used resins belong to the acrylic materials. The more widely used bone cements are composed of two phases, a liquid phase substantially composed of methyl methacrylate with an addition of N,N-dimethyl-p-toluidine as accelerator and hydroquinone as stabilizer, and a solid phase composed of a dry powder substantially composed of poly(methyl methacrylate) with a peroxide, usually benzoyl peroxide, as polymerization initiator. At the moment of use, the two phases are mixed, the polymer powder representing the solid phase is dissolved in the monomer present in the liquid phase, giving a liquid viscous solution. In the meantime, the N,N-dimethyl-p-toluidine causes the peroxide to decompose with the formation of free radicals which initiate the polymerization reaction, resulting in hardening of the mixture.

In addition to poly(methyl methacrylate), bone cements are known which contain a solid phase containing resins of the poly(ethyl methacrylate), poly(butyl methacrylate), poly(methyl methacrylate/styrene) types and/or copolymers thereof, which belong to the class of acrylic resins.

The effect of the bone cement consists in completely filling the voids present between the prostheses and the bone cavity prepared for implantation thereof, so as to ensure mechanical anchoring and a perfect fit of the bone implant.

The mechanical strength of the hardened cement thus obtained is not as high as that of the original bone tissues. Indeed, as a result of the considerable loads or as a result of fatigue stress at a high cycle number, the bone cement fillings can give way and fracture. The modification of such fillings with time, their eventual flaking-off and their mechanical weakening must therefore be able to be detected and monitored, for example using standard radiological and tomographic techniques.

Since the synthetic base resin is transparent to X-rays, the bone cement must be rendered opaque by adding suitable inorganic biocompatible substances.

The opacity to X-rays of the elements increases substantially in proportion to their atomic weight. In general, especially for the heavier elements, their toxicity also increases. In medicine the known and most commonly used contrast agents are iodine, either in elemental or bonded form, bismuth in the form of carbonate and barium in the form of sulphate.

By using compounds such as salts or oxides, the radiopaque element constitutes only a portion of the additive. For example, the metal amounts to only 58% of barium sulphate, the remaining material being substantially transparent to X-rays.

In the known bone cements, such radiopacifying materials usually consist of barium sulphate or zirconium oxide additives, in an amount of about 10% by weight, relative to the dry polymer.

Such additives, which introduce discontinuities in the polymer, weaken further the mechanical properties of the hardened cement, increasing the risk of failure and frequency of fracturing or flaking off.

With the aim of reducing such disadvantages, the teachings of U.S. Pat. No. 5,795,922 propose encapsulation of the radiopacifying substance, in this case selected from the group consisting of barium salts, zirconium oxide and bismuth glasses, in microcapsules of a compatible polymer material. During formation of the bone cement, the polymer material dissolves completely in the liquid phase releasing its contents, the radiopaque substance, which is enveloped by the polymer being formed.

These known bone cements are not suitable for the treatment of certain disorders, for example, in the case of vertebroplasty.

Indeed, in the case of disorders of the general tumour type, in which an emptying of the vertebra structure is produced, the latter loses its mechanical strength and collapses under the body weight, resulting in crushing of the nerve endings, causing intense suffering of the patient and a partial loss of motor function.

At the present time, in accordance with the prior art hitherto, such disorders are treated with prostheses, metal plates or by administering analgesics.

A further known technique for such disorders consists in opening the vertebra, introducing the bone cement of the type described above, and closing it again. The hardened bone cement substitutes the missing part of the vertebra.

Recently, a new technique has been proposed which consists in injecting liquid bone cement, by means of a needle, inside the vertebra, thus avoiding the invasive surgical intervention referred to above.

This technique requires the use of a low-viscosity liquid bone cement so as to be able to inject it easily by means of a needle which may have a diameter of even less than 2 mm.

This operation is complicated and not free of risks since an error in positioning of the cement could result in a contact of the resin with the nerve endings of the spinal column, resulting in a paralysis of the patient or in a substantial increase in pain, owing to the insertion of protrusions in direct contact with the nerve centers which pass through the spinal column.

In order to be able to perform this operation with absolute safety, the surgeon must be well-informed of the state of progress of the injection, which is controlled in real time by means of X-rays. Since the time during which monitoring must take place is quite long, usually several hours, the intensity of exposure to the radiation must be extremely low. Accordingly, it is not possible to use radiological or tomographic techniques involving significant radiation doses, but instead fluoroscopic techniques in which the patient is subjected to low-intensity X-rays must be used.

The known bone cements described above, which are particularly suitable for the fixing of prostheses, have proved to be insufficiently opaque to low-intensity X-rays, poorly visible, practically transparent and substantially unsuitable for performing the injection with adequate safety.

The medico-scientific literature has reported several cases in which the surgeon has added an appreciable quantity of the radiopacifying contrast agent barium sulphate of up to 30–40% by weight, so as to render the cement used sufficiently radiopaque.

On the other hand, the use of a metal in the form of salt has the consequence that only 58% by weight of the material introduced has an actual radiopacifying effect.

The presence of a voluminous quantity of powdery radiopacifier in the acrylic matrix increases the probability of initiating fractures and thus undermines the integrity of the structure and jeopardizes the mechanical strength of the material in the long run (fatigue strength). This phenomenon is confirmed even in those cases in which the static performances comply with the minimum requirements of the ISO standard 5833.

In any case, this benefits the patient, but the intervention cannot guarantee that the expected result will be maintained over a long period, since the reinforcing structure is extremely weak.

The medico-scientific literature has described other cases in which the surgeon adds to the bone cement of the type described above containing approximately 10% by weight of barium sulphate, relative to the dry polymer, or approximately 15% by weight of zirconium oxide, relative to the dry polymer, a quantity of powdery tungsten amounting to about 2% by weight as further radiopacifier.

The addition of about 9% by weight of tantalum powder to a bone cement devoid of radiopacifiers is likewise known.

In all abovementioned cases, the addition is made directly by the surgeon, shortly before the intervention, under his responsibility and using a non-certified material. This has made it possible to improve the radiopacifying effect without decreasing excessively the mechanical properties of the resulting acrylic cement.

Nevertheless, the latter bone cements have also proved to be not without drawbacks. A first disadvantage is the fact that powdery tantalum, in contrast to tantalum in plaque form, is not considered biocompatible according to current regulations. The biocompatibility of tantalum is related to oxygen absorption, a phenomenon which is increased by the considerable specific surface area of the finely divided form necessary for efficient dispersion in the acrylic cement. Even if the cement is prepared immediately before use, it is almost impossible to prevent the oxygen from being absorbed by the metal and to keep its level at values below 300 ppm as required by the current regulations (ISO 13782), and the use of tantalum oxide is prohibited by the Pharmacopoeia.

A second drawback consists in the fact that the tantalum powder must be prepared by the surgeon at the moment of using it since, due to the sterility and biocompatibility requirements mentioned above, it is practically impossible to purchase tantalum powder in sterile form on the market.

A further drawback consists in the fact that it is difficult to obtain a diameter distribution of the particles forming the fine powder suitable for injection by means of a syringe.

A further drawback consists in the fact that the dispersion phase of the tantalum powder has the tendency to form inclusions of air in the bone cement.

A further drawback consists in the fact that it is extremely difficult to obtain a homogeneous dispersion of the powder in the polymer matrix.

International Patent Publication No. WO-A-9204924 discloses a radiopaque bone cement comprising a solid phase of polymethylmethacrylate powder and a liquid phase of polymethylmethacrylate monomer, wherein added to the solid phase are particles of radiopaque material coated with polymethylmethacrylate before mixing with the liquid phase. The radiopaque material is zirconium oxide or barium sulfate having diameter from 1 µm and 250 µm. However, the use of zirconium oxide or barium sulfate as radiopaque materials does not permit improvement of radiopacity combined with increased mechanical strength and fatigue resistance as specifically required for vertebroplasty. Moreover, the coating layer applied to the radiopaque materials of this prior art is aimed at avoiding the porosity and non-uniformity of the cement and therefore is not purported to prevent the formation of oxides.

International Patent Publication No. WO-A-9918894 discloses a bone cement specifically intended for vertebroplasty wherein the radiopaque material comprises particles of barium sulfate, tungsten or tantalum and therefore exhibits higher radiopacity as compared with the known bone cement compositions. However, the surface of the tungsten and/or tantalum particles used in Publication No. WO-A-9918894 is free of protection and has no coating to prevent oxygen absorption, and accordingly, some embodiments of this bone cement may be prohibited by the Pharmacopoeia. Morover, WO-A-9918894 gives no indication of the form of protection of the tungsten and/or tantalum particles used as radiopacifying agent.

OBJECTS OF THE INVENTION

A general object of the present invention consists in eliminating the drawbacks of the abovementioned prior art by providing an acrylic bone cement which exhibits improved radiopacity and mechanical strength properties.

A particular object is to provide an acrylic bone cement which has improved mechanical strength properties, in particular better fatigue behavior, compared to the known bone cements of the past.

A particular object is to provide an acrylic bone cement which has improved radiopacity properties without the addition of additives consisting only in part of radiopacifiers.

Another particular object of the present invention is to provide a liquid acrylic bone cement, prepared with biocompatible materials without a reduction in biocompatibility.

A further object of the present invention is to provide a liquid acrylic bone cement, prepared in sterile fashion using a sterile or readily sterilizable material.

Another further object of the present invention is to provide an acrylic bone cement which is particularly suitable for vertebroplasty.

Yet Another object of the present invention is to provide a method for the preparation of an acrylic bone cement which is relatively easy for the surgeon to perform.

SUMMARY OF THE INVENTION

The aforementioned objects, together with others that will become more apparent hereinafter, are achieved by means of a radiopaque acrylic bone cement for orthopaedic use that exhibits considerable radiopacity, which is achieved by adding a limited amount of a radiopaque contrast agent.

Furthermore, the bone cement possesses mechanical properties which are considerably better than those of the prior art, in which the contrast element is added, but not bonded to the polymer matrix and constitutes an initiating element for fracturing of the polymerized mass.

In the method for preparation of the bone cement, the polymer coating layer of the metal defines at the moment of polymerization a zone of chemical adhesion between the polymer chains being formed and the metal particles. This determines the increase in mechanical properties of the composite in which the metal particles are no longer an element which is not bonded to the polymer matrix.

This makes it possible to take advantage of the higher ductility of the metallic material compared to the fragility of the polymer material, imparting to the composite as a whole better mechanical properties, especially a better tenacity and fatigue strength.

A further advantage of the bone cement according to the invention consists in the fact that the biocompatible and sterilizable polymer coating layer protects each single tantalum or tungsten metal particle contained in the mixture from exposure to oxygen. This prevents the oxygen from being absorbed, thus avoiding the formation of oxides and overcoming the drawbacks and pharmacological limitations linked to the presence of oxygen.

Even after addition of the solid phase to the liquid phase, this coating, owing to the fact that it is not dissolved completely, retains its function as barrier and protector of the metal present therein.

Moreover, the bone cement can be delivered in the same package as the contrast agent and added directly by the manufacturer to the solid phase in the optimum amount and diametral distribution for the desired application as sterile medical remedy.

A further advantage of the invention is that it is possible to add to the bone cement active substances, which will be released in-situ for the treatment of possible disorders.

A further advantage of the bone cement according to the invention is that it can be formulated with such a fluidity that it can be administered through a cannula having an internal diameter of less than 2 mm.

The device according to the present invention can advantageously be used for the filling of deep and critical bone holes by means of operations with limited invasiveness, for example, using percutaneous techniques. Moreover, the use can be extended to zones in which high radiopacity and mechanical properties, not satisfied by the known bone cements, are required.

Using the radiopaque acrylic bone cement according to the invention it is possible, for example, to perform vertebroplasty interventions under absolutely safe conditions, with continuous monitoring of the operation, achieved by administering to the patient a limited amount of X-rays and obtaining a hardened support having considerable mechanical strength with respect to the stresses induced during walking.

BRIEF DESCRIPTION OF THE DRAWINGS

Further features and advantages of the invention will be more clearly understood from the detailed description of several preferred, but not exclusive embodiments of the radiopacified acrylic bone cements, furnished by way of a non-limiting example, with reference to the accompanying drawings, in which.

DETAILED DESCRIPTION OF THE PREFERRED EMBODIMENTS

A radiopaque acrylic bone cement for orthopaedic use according to the invention essentially comprises a solid phase dissolved in a liquid phase.

The solid phase is essentially composed of a mixture of at least one acrylic polymer, for example based on poly(methyl methacrylate), at least one free-radical polymerization initiator and at least one or more substances which are opaque to X-rays. More specifically, the mixture can contain poly (methyl methacrylate), poly(methyl methacrylate/styrene), poly(butyl methacrylate) and copolymers thereof and benzoyl peroxide as initiator. Moreover, the solid-phase mixture may contain one or more pharmacologically active substances.

The liquid phase is essentially composed of a mixture of a monomer, at least one accelerator and at least one stabilizer. More specifically, the monomer can consist of monomethylmethacrylate and the accelerator can consist of N,N-dimethyl-p-toluidine.

Figure 1:
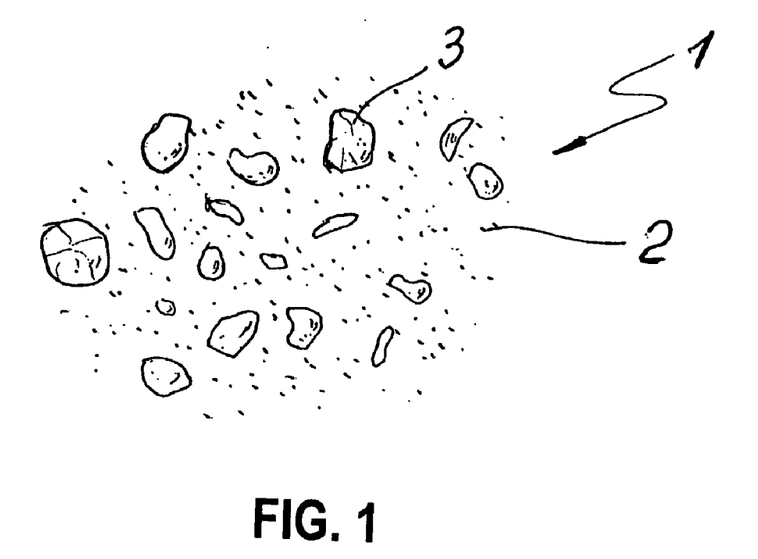
FIG. 1 shows a schematic representation of the bone cement.

Referring to FIG. 1, the hardened bone cement, indicated overall by 1, is composed of a polymer matrix 2 in which irregularly shaped particles 3 composed of radiopaque elements 4 coated with a polymer compatible with the polymer matrix 2 are dispersed homogeneously.

Figure 2:
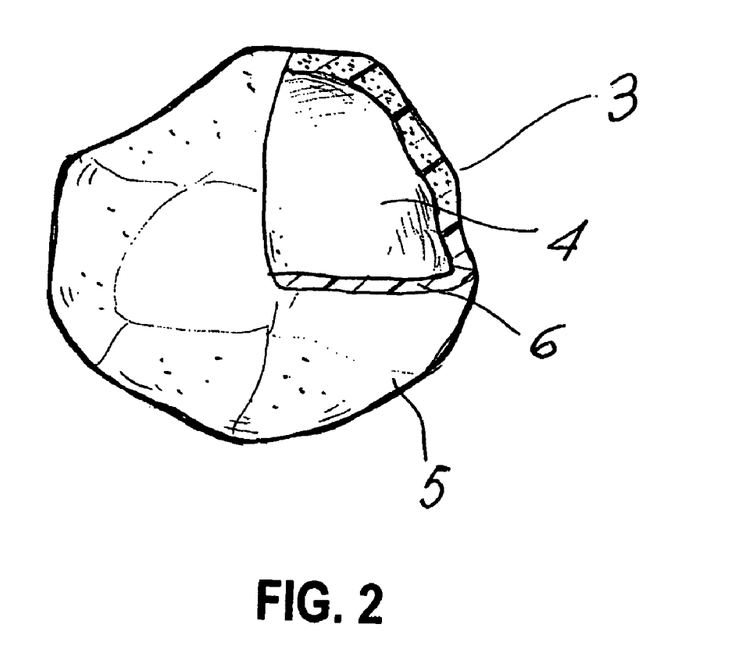
FIG. 2 shows a partially sectioned view of a radiopaque metal particle coated with a poly(methyl methacrylate)-based protective polymer.
Figure 3:
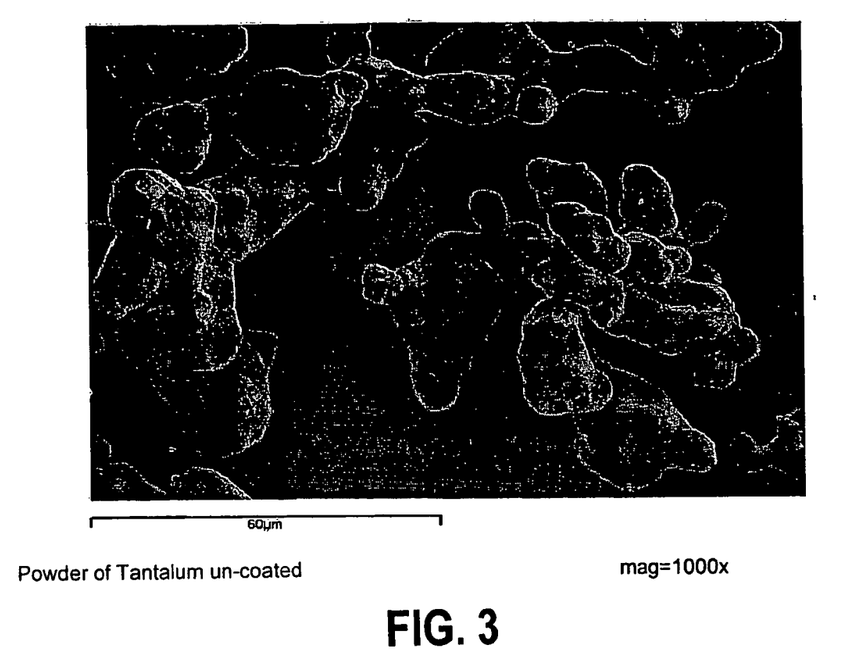
FIG. 3, FIG. 4 and FIG. 5 show SEM (Scanning Electron Microscope) pictures of different amplification, i.e., 1000×, 3000× and 10,000× respectively, of the radiopaque tantalum metal particles as obtained before being coated with the protective polymer.
Figure 4:
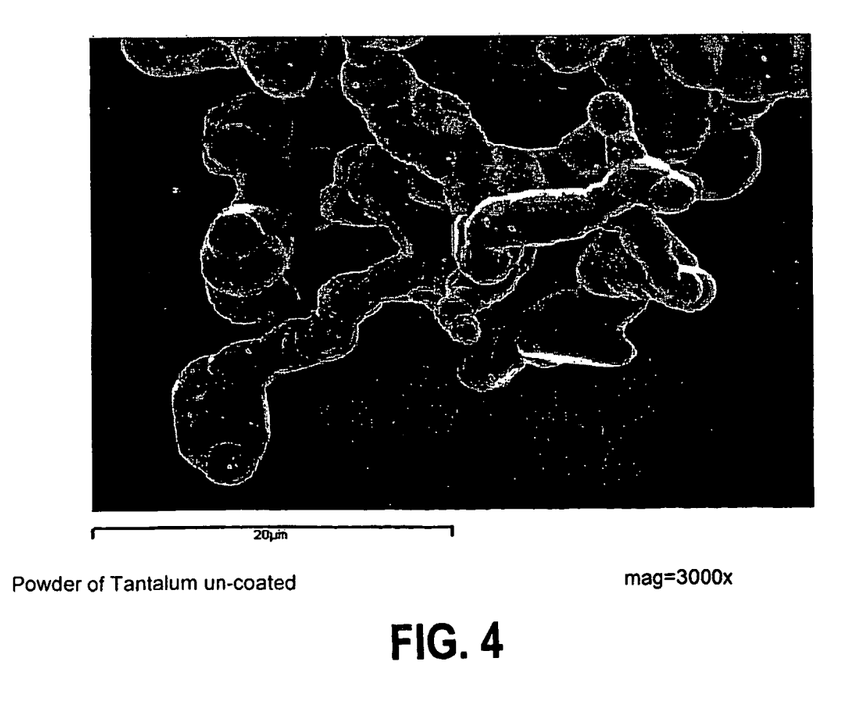
Figure 5:
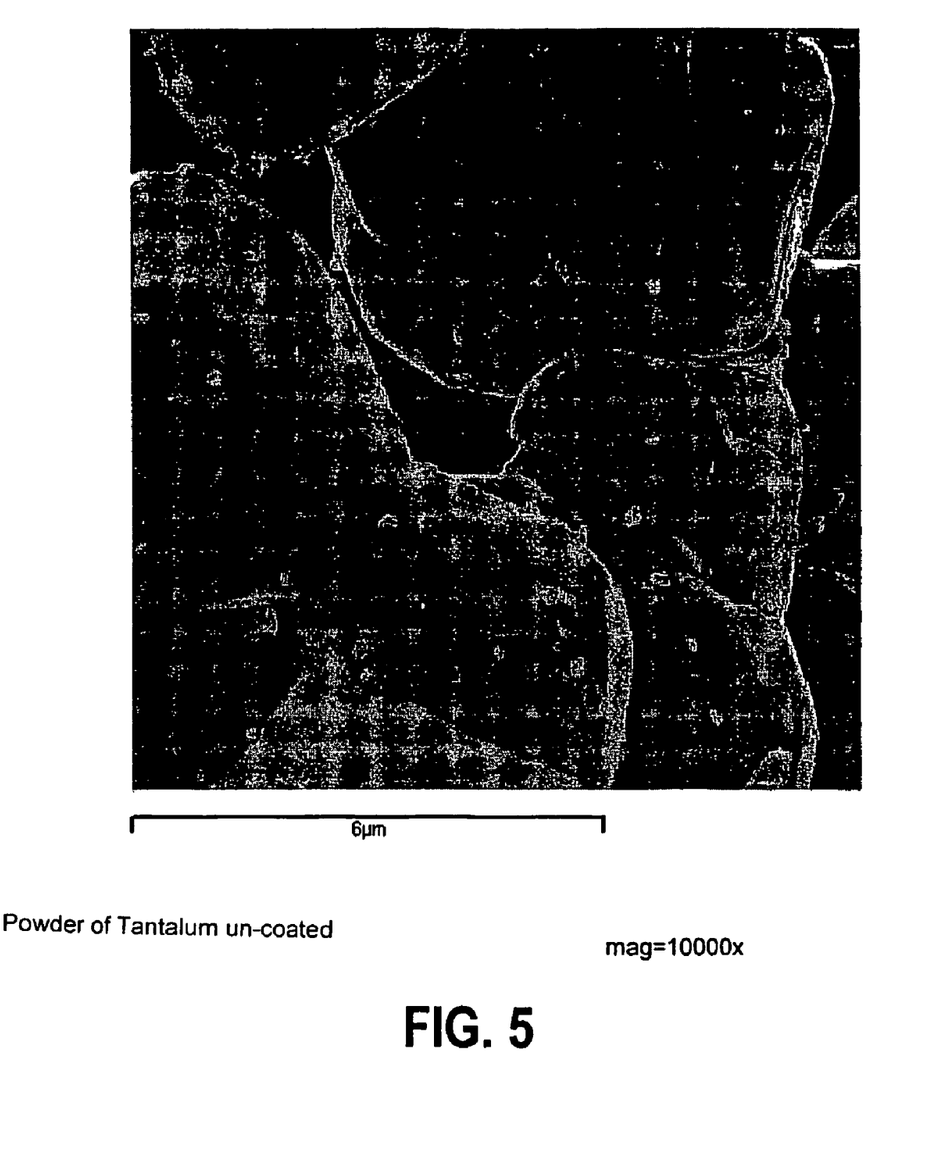
Figure 6:
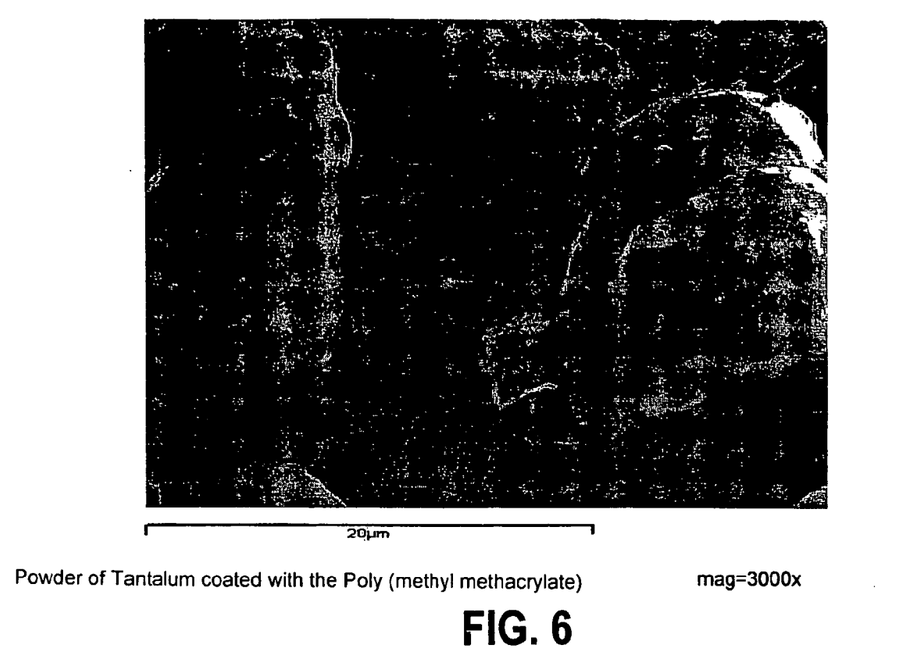
FIG. 6 and FIG. 7 show SEM (Scanning Electron Microscope) pictures of different amplifications, i.e., 3000× and 10,000×, respectively, of the radiopaque tantalum metal particles coated with protective polymer.
Figure 7:
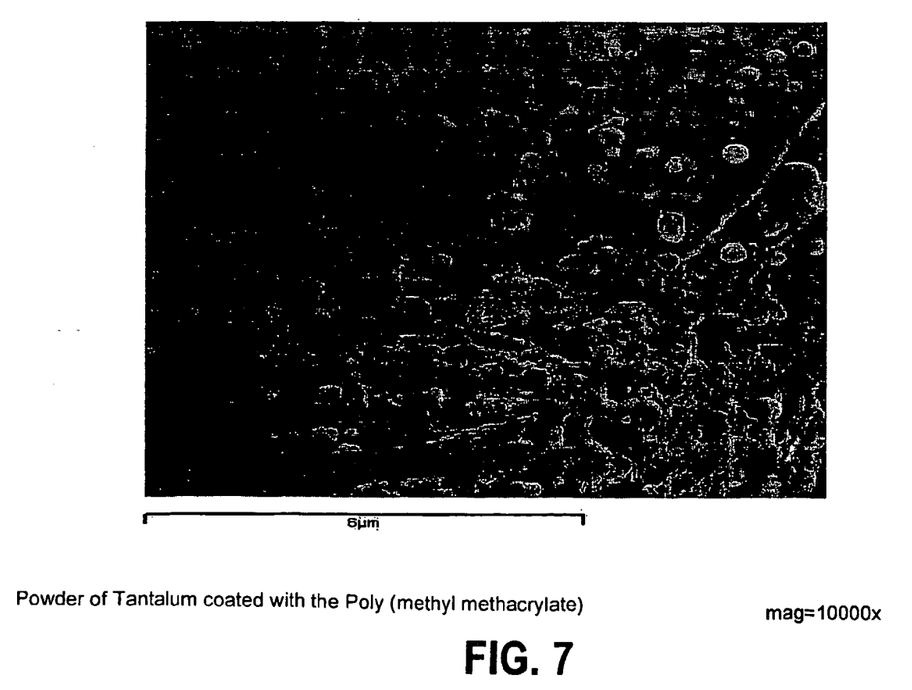

The irregularly shaped particle 3, shown schematically in FIG. 2, is composed of the radiopaque element 4 completely coated with a polymer layer 5 compatible with the matrix 2 and having such a thickness 6 that it does not dissolve completely in the liquid phase during polymerization.

A particular characteristic of the present invention consists in adding radiopaque elements of high molecular weight, greater than 130 Dalton, in the form of metals, mixtures of metals, or metal compounds such as alloys. Indeed, many elements of high atomic weight, for example more than 125 Dalton, are highly radiopaque and thus suitable for use as long as they are non-toxic or can be used in non-toxic form.

Preferably, the radiopaque substances contained in the solid phase comprise tungsten and/or tantalum particles in the form of metals, compounds or mixtures thereof, which particles are covered with a coating layer of a polymer compatible with said bone cement. In place of tantalum or tungsten, it is also possible to use other metals of high atomic weight such its gold, platinum, bismuth or lead.

Ideally the coating layer of the particles is an acrylic polymer based on poly(methyl methacrylate).

Advantageously, the coating layer can be obtained by adding the polymer based on poly(methyl methacrylate), dissolved in a water-miscible solvent, to an aqueous dispersion of the metal particles from which the surface layer had previously been removed, followed by evaporation of the solvents and drying of said layer.

The oxygen content of the tantalum metal is preferably less than about 300 ppm.

The diameter of the radiopaque particles coated with poly(methyl methacrylate) can be between 1 μm and 150 μm.

Before depositing the coating, the diameter of radiopacifying metal particles can be between 1 μm and 100 μm.

Prior to the deposition of the coating, the radiopacifying particles can have nanometer size, for example, a diameter between 25 nanometres and 1000 nanometres. In this manner, the diameter of the coated radiopacifying particles, which have a plurality or an aggregate of nanometer-sized metal particles, can be between 20 μm and 60 μm, with the noteworthy advantage of a more homogeneous and easier dispersion of said particles in the polymer powder.

Ideally said nanometer-sized metal particles may have been pre-sinterized.

Preferably, the tantalum or tungsten to poly(methyl methacrylate) weight ratio in the particles is between 95/5 and 70/30.

The molecular weight of the particle coating polymer can advantageously be between 20,000 and 800,000 Dalton.

The amount of radiopacifying element can advantageously vary between 1% and 20% by weight, relative to the solid phase, and is preferably between 2% and 5% by weight, relative to the solid phase.

Advantageously, the solid phase and the coated radiopaque particles can be contained in the same package. Alternatively, the solid phase and the coated radiopaque particles can be contained in different packages.

In the case of a single package, it can consist of a shell containing both the solid phase and the liquid phase. In clinical use, the cement-containing shell is opened, and its contents consisting of an envelope containing the powder and the vial containing the liquid phase is transferred to the operating room aseptically on a sterile shelf.

In preparing the cement, the ampule is opened, and the entire liquid is placed in the mixing bowl, and all the powder is introduced into the liquid. In order to minimize the inclusion of bubbles, the cement must be mixed by moving the spatula from the outside to the center of the bowl. Since the whole powder must be impregnated with liquid, any solid residues not impregnated with liquid are carefully immersed in the moist mass using the spatula.

At this point, the liquid mass can be transferred into a syringe for in-situ injection.

The radiopacifying powder according to the present invention can be mixed with the solid phase of the bone cement system.

Table 1 shows a few indicative but not exhaustive examples of preferred formulations.

TABLE 1

|  | Liquid phase (Values in percent by weight) |  | Solid phase (Values in percent by weight) |  |
|---|---|---|---|---|
| Cemex RX (reference) | Methyl methacrylate | 98.20 | Poly(methyl methacrylate) | 88.00 |
|  | N,N-dimethyl-p-toluidine | 1.80 | Benzoyl peroxide | 3.00 |
|  | Hydroquinone | 75 ppm | Barium sulphate FU | 9.00 |
| Cemex XL (reference) | Methyl methacrylate | 98.20 | Poly(methyl methacrylate) | 85.00 |
|  | N,N-dimethyl-p-toluidine | 1.80 | Benzoyl peroxide | 3.00 |
|  | Hydroquinone | 75 ppm | Barium sulphate FU | 12.00 |
| Example 1 (reference) | Methyl methacrylate | 98.20 | Poly(methyl methacrylate) | 82.5 |
|  | N,N-dimethyl-p-toluidine | 1.80 | Benzoyl peroxide | 3.00 |
|  | Hydroquinone | 75 ppm | Barium sulphate FU | 12.00 |
| Example 2 (reference) | Methyl methacrylate | 98.20 | Tantalum as-delivered Poly(methyl methacrylate) | 2.50 67.00 |
|  | N,N-dimethyl-p-toluidine | 1.80 | Benzoyl peroxide | 3.00 |
|  | Hydroquinone | 75 ppm | Barium sulphate FU | 30.00 |
| Example 3 | Methyl methacrylate | 98.20 | Poly(methyl methacrylate) | 82.00 |
|  | N,N-dimethyl-p-toluidine | 1.80 | Benzoyl peroxide | 3.00 |
|  | Hydroquinone | 75 ppm | Barium sulphate FU | 10.00 |
|  |  |  | PMMA-coated tantalum | 5.00 |
| Example 4 | Methyl methacrylate | 98.20 | Poly(methyl methacrylate) | 82 |
|  | N,N-dimethyl-p-toluidine | 1.80 | Benzoyl peroxide | 3.00 |
|  | Hydroquinone | 75 ppm | Barium sulphate FU | 12.50 |
|  |  |  | PMMA-coated tantalum | 2.50 |
| Example 5 | Methyl methacrylate | 98.20 | Poly(methyl methacrylate) | 87 |
|  | N,N-dimethyl-p-toluidine | 1.80 | Benzoyl peroxide | 3.00 |
|  | Hydroquinone | 75 ppm | PMMA-coated tantalum | 10.00 |
| Example 6 | Methyl methacrylate | 98.20 | Poly(methyl methacrylate) | 82 |
|  | N,N-dimethyl-p-toluidine | 1.80 | Benzoyl peroxide | 3.00 |
|  | Hydroquinone | 75 ppm | Zirconium oxide | 10.00 |
|  |  |  | PMMA-coated tantalum | 5.00 |
| Example 7 | Methyl methacrylate | 98.20 | Poly(methyl methacrylate) | 80 |
|  | N,N-dimethyl-p-toluidine | 1.80 | Benzoyl peroxide | 3.00 |
|  | Hydroquinone | 75 ppm | Zirconium oxide | 14.50 |
|  |  |  | PMMA-coated tantalum | 2.50 |
| Example 8 | Methyl methacrylate | 98.20 | Poly(methyl methacrylate) | 86 |
|  | N,N-dimethyl-p-toluidine | 1.80 | Benzoyl peroxide | 3.00 |
|  | Hydroquinone | 75 ppm | Barium sulphate FU | 8.50 |
|  |  |  | PMMA-coated tungsten | 2.50 |
| Example 9 | Methyl methacrylate | 98.20 | Poly(methyl methacrylate) | 82.00 |
|  | N,N-dimethyl-p-toluidine | 1.80 | Benzoyl peroxide | 3.00 |
|  | Hydroquinone | 75 ppm | Barium sulphate FU | 10.00 |
|  |  |  | PMMA-coated tungsten | 5.00 |
| Example 10 | Methyl methacrylate | 98.20 | Poly(methyl methacrylate) | 82 |
|  | N,N-dimethyl-p-toluidine | 1.80 | Benzoyl peroxide | 3.00 |
|  | Hydroquinone | 75 ppm | Barium sulphate FU | 12.50 |
|  |  |  | PMMA-coated tungsten | 2.50 |

Using the bone cements prepared by the abovementioned methodology and the formulations listed in Table 1, in accordance ISO standard 5833, ASTM standard F451-99 and ISO standard 527, a few samples were prepared for measuring the compressive strength, the tensile strength, the bending strength and the work at break. The latter, expressed in MJ/m$^3$, is calculated as the integral of the stress/deformation curve obtained in the bending test.

Tables 2, 3 and 4 list the values, expressed in MPa, obtained with the samples.

TABLE 2

|  | Compression | Standard deviation | Tensile strength | Standard deviation |
|---|---|---|---|---|
| Cemex RX (reference) | 106 | 7.75 | 36 | 4.20 |
| Example 1 | 108 | 3.51 | 38 | 1.04 |
| Example 3 | 131 | 6.68 | 44 | 0.14 |
| ISO 5833 | >70 |  | >30* |  |

*Limit not present in the regulations

TABLE 3

|  | Bending | Standard deviation | Modulus of Elasticity | Standard deviation |
|---|---|---|---|---|
| Cemex RX (reference) | 61 | 4.78 | 2974 | 64 |
| Example 1 | 62 | 2.09 | 2850 | 334 |
| Example 3 | 70 | 5.19 | 2909 | 102 |
| ISO 5833 | >50 |  | >1800 |  |

TABLE 4

|  | Deformation at break (%) | Standard deviation | Work at break (MJ/m$^3$) | Standard deviation |
|---|---|---|---|---|
| Cemex RX (reference) | 2.01 | 0.17 | 0.88 | 0.14 |
| Example 2 | 2.22 | 0.23 | 0.79 | 0.22 |
| Example 3 | 2.72 | 0.39 | 1.11 | 0.31 |

The tests were carried out at ambient temperature and humidity. The samples, prepared according to ISO 5833, were kept in water at 37° C. for 48 hours, taken out a few minutes prior to the test and deformed at a set speed of 20 mm/min for the compression measurements, 10 mm/min for the tensile measurements, and 5 mm/min for the bending stress measurements.

The work at break of the bone cement according to the present invention shows an increase of 26%, relative to the value of conventional bone cement and of 40%, compared to the bone cement made radiopaque by addition of a vast amount (30%) of barium sulphate.

Using the bone cements prepared by the abovementioned methodology and the formulations listed in Table 1, the values of the chemical and physical properties such as viscosity, flow behavior, doughing time, setting time and the maximum polymerization temperature were measured according to ISO standard 5833:92 and ASTM standard F451-99. The values obtained are listed in Tables 5 and 6.

TABLE 5

|  | Viscosity $\eta'_4$ (Pa*s) | Doughing time (DT) (min) | Setting time (ST) (min) | Maximum temperature (° C.) |
|---|---|---|---|---|
| Cemex XL | 13,900 ± 2970 | 4'55" | 12'50" | 64 |
| Example 4 | 27,000 ± 1414 | 9'30" | 16'00" | 72 |
| ISO 5833 |  | <5' | <15' | <90 |

The value $\eta'_4$, of the apparent dynamic viscosity at 4' from mixing, measured at 22° C. and a humidity of 32%, is customarily taken as a descriptive parameter of the rheological behavior of the material.

The measurements of DT, ST and the maximum polymerization temperature were performed in a laboratory temperature-controlled at 23° C.±1 and at a relative humidity greater than 40%, using material which, in turn, was left in a thermostat under the same conditions for at least 16 hours.

TABLE 6

|  | Flow behaviour (g) | Standard deviation | % by weight |
|---|---|---|---|
| Cemex XL | 60.5 | 0.70 | 89 |
| Example 4 | 58 |  | 85 |

The flow behavior represents the mass of cement, expressed in grams, which flows from the inclined mixing bowl at 90° C. in 60 seconds after 1' and 30" from the beginning of mixing.

The bone cement according to the present invention exhibits very high properties in all stress directions, and in particular the metal additive improves the compressive strength.

In all cases, the materials have exceeded the limits required by the regulations and thus, from a mechanical point of view, fall entirely within the class of bone cements.

The polymerization temperature is increased in the tantalum material even though it is still substantially below the values required by the standards.

It must be pointed out that the bone cement according to the invention can advantageously be used for surgical interventions in vertebroplasty by means of percutaneous in-situ injection of the cement or else for surgical interventions of osteosynthesis in which superior radiopacity and mechanical properties are required.

What is claimed is:

1. Radiopaque acrylic bone cement for orthopedic use, comprising a solid phase essentially composed of a powder of at least one acrylic polymer, one free-radical polymerization initiator and one radiopacifying material, and a liquid phase substantially composed of a mixture of at least one monomer, one accelerator and one stabilizer, said solid phase being capable of hardening upon mixing thereof with said liquid phase so as to give a bone cement matrix, wherein said radiopacifying material comprises particles of metals having molecular weight equal to or higher than 130 Dalton, mixtures, alloys or compounds thereof, which particles are covered with a coating layer of a polymer which is compatible with said matrix, wherein said metal particles comprise tantalum and/or tungsten particles, said polymer coating layer covering each of said metal particles to protect them from exposure to oxygen, said coating layer being so sized that it does not completely dissolve in said liquid phase during polymerization of said bone cement so as to keep its oxygen barrier properties.

2. Acrylic bone cement according to claim 1, wherein said metals of high molecular weight are selected in such a way as to have an oxygen content of less than 300 ppm by weight.

3. Acrylic bone cement according to claim 1, wherein said coating layer of said metal particles is a polymer taken from the group consisting of poly(methyl methacrylate), poly(methyl methacrylate/styrene), poly(butyl methacrylate) and copolymers thereof.

4. Acrylic bone cement according to claim 1, wherein each single uncoated metal particle has an average diameter of between 1 μm and 100 μm.

5. Acrylic bone cement according to claim 1, wherein each single coated metal particle has an average diameter of between 1 μm and 150 μm.

6. Acrylic bone cement according to claim 1, wherein said polymer coating layer covers an aggregate of previously synthesized nanometer-sized metal particles.

7. Acrylic bone cement according to claim 6, wherein said metal particles of said aggregate have an average diameter of between 25 nm and 1000 nm.

8. Acrylic bone cement according to claim 1, wherein the molecular weight of the coating polymer of said particles which is compatible with said bone cement is between 20,000 and 800,000 Dalton.

9. Acrylic bone cement according to claim 1, wherein the molecular weight of the coating polymer of said particles which is compatible with said bone cement is between 300,000 and 800,000 Dalton.

10. Acrylic bone cement according to claim 1, wherein the weight ratio between the metal contained in said particles and their coating polymer is between 95:5 and 70:30.

11. Acrylic bone cement according to claim 1, wherein the amount of the radiopacifying material is between 1% and 20% by weight, relative to said solid phase.

12. Acrylic bone cement according to claim 11, wherein the amount of radiopacifying material is between 2% and 5% by weight, relative to said solid phase.

13. Acrylic bone cement according to claim 1, wherein said solid phase further comprises one or more pharmacologically active substances.

14. Acrylic bone cement according to claim 1, wherein said solid phase and said coated radiopaque particles are contained in the same package.

15. Acrylic bone cement according to claim 1, wherein said solid phase and said coated radiopaque particles are contained in separate packages.

16. Acrylic bone cement according to claim 1, wherein said at least one acrylic polymer is taken from the group consisting of poly(methyl methacrylate), poly(methyl methacrylate/styrene), poly(butyl methacrylate) and copolymers thereof.

17. Method for preparing a radiopaque acrylic bone cement for orthopedic use, comprising the steps of:
    preparing a solid phase essentially composed of a powder of at least one acrylic polymer, one free-radical polymerization initiator and one radiopacifying material;
    preparing a liquid phase composed of a mixture of at least one monomer, one accelerator and one stabilizer;
    mixing said solid phase with said liquid phase so as to perform polymerization in such a way that a bone cement matrix is obtained; and
    wherein the radiopacifying material is obtained by preparing a powder of metal particles of molecular weight equal or higher than 130 Dalton, mixtures, alloys or compounds thereof, said metal particles comprising tantalum and/or tungsten particles, and coating said particles with a layer of a polymer which is compatible with said matrix, said polymer coating layer being so selected to protect said metal particles from exposure to oxygen, said polymer coating layer being so sized that it does not completely dissolve in said liquid phase so as to keep its oxygen barrier properties.

18. Method according to claim 17, wherein said metal particles, before being coated, are subjected to a step of removal of their surface layer.

19. Method according to claim 17, wherein said coating layer of said metal particles is obtained by adding said polymer, dissolved in water-miscible organic solvents, to an aqueous dispersion of said radiopaque particles, followed by evaporation and drying of said solvents.

20. Method according to claim 17, wherein said at least one acrylic polymer is taken from the group consisting of poly(methyl methacrylate), poly(methyl methacrylate/styrene), poly(butyl methacrylate) and copolymers thereof.

* * * * *